United States Patent [19]

Moretti

[11] 4,311,650
[45] Jan. 19, 1982

[54] MULTI-STAGE NEUTRALIZATION OF SULFATED COMPOUNDS

[75] Inventor: Giovanni Moretti, Milano San Felice, Italy

[73] Assignee: Ballestia Chimica, S.p.A., Italy

[21] Appl. No.: 156,422

[22] Filed: Jun. 4, 1980

[30] Foreign Application Priority Data

Jun. 15, 1979 [IT] Italy .............................. 12643 A/79

[51] Int. Cl.³ .................. C07C 141/04; C07C 141/08
[52] U.S. Cl. ............................ 260/458 R; 260/459 R
[58] Field of Search ....................... 260/458 R, 459 R

[56] References Cited

U.S. PATENT DOCUMENTS 4,153,625  5/1979  Barton et al. .................. 260/459 R

*Primary Examiner*—Nicky Chan
*Attorney, Agent, or Firm*—Robert E. Burns; Emmanuel J. Lobato; Bruce L. Adams

[57] ABSTRACT

This invention relates to a process for the multi-stage neutralization of sulfated compounds, particularly sulfuric acids obtained by sulfating alcohols.

8 Claims, 1 Drawing Figure

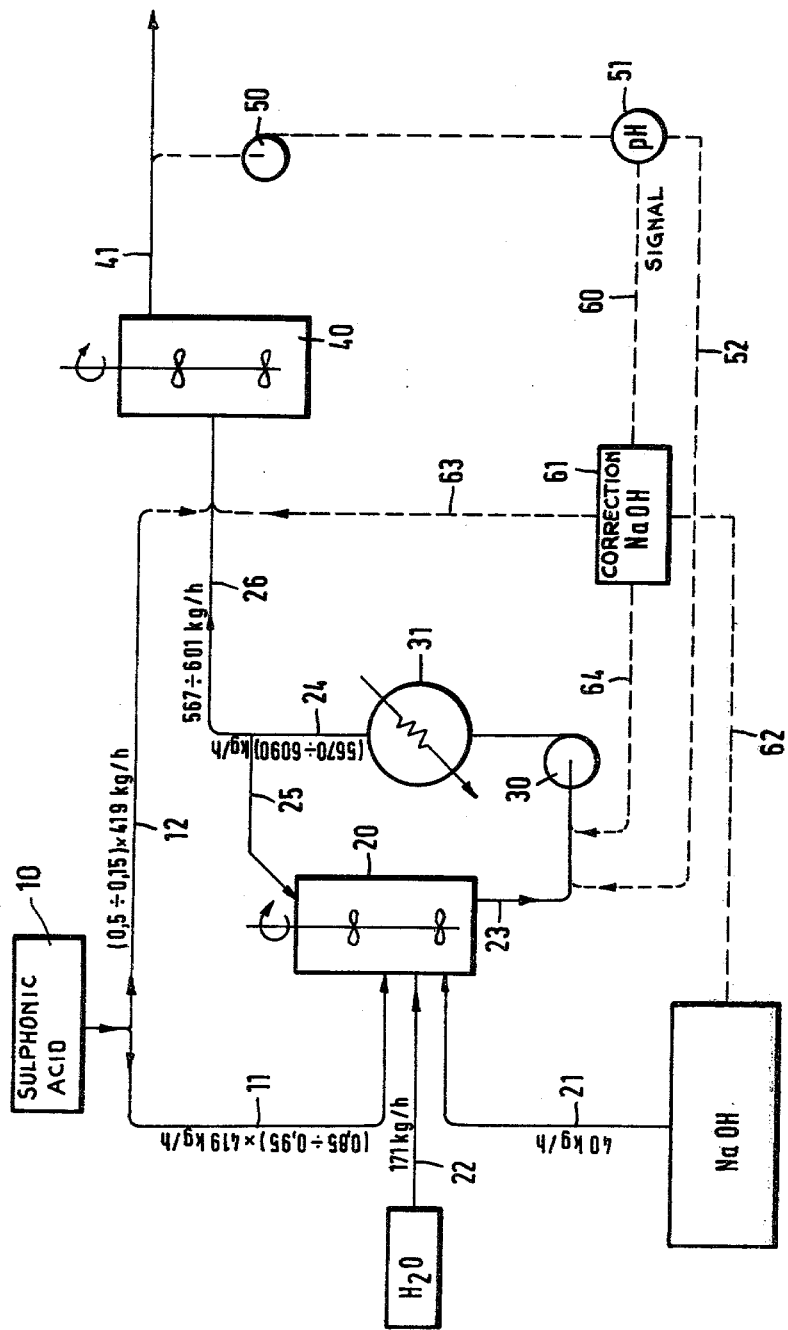

MULTI-STAGE NEUTRALIZATION OF SULFATED COMPOUNDS

BACKGROUND OF THE INVENTION

The neutralization of sulfated alcohols in a single stage, as is carried out in the known art, requires extreme stirring and cooling conditions in order to prevent local phenomena (at the micellar level) in the form of temperature increase and/or preferential contact of the monoester of sulfuric acid with the dilution water and/or reaction with consequent degradation. This degradation can be represented by the following reactions:

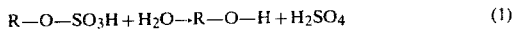
$$R-O-SO_3H + H_2O \rightarrow R-O-H + H_2SO_4 \quad (1)$$

$$2 R-O-SO_3Na + H_2SO_4 \rightarrow ROSO_3H + Na_2SO_4 \quad (2)$$

wherein R indicates the alcohol radical. The first term of the left-hand side of reaction (1) is therefore a monoester of sulfuric acid. The first term of the right-hand side of reaction (1) is the initial alcohol obtained by degradation of the monoester of sulfuric acid in contact with the water present in the reaction mixture. As can be seen, the regression of the monoester of sulfuric acid to alcohol is accompanied by the formation of sulfuric acid. Reaction (1) is favoured by increased contact time between the monoester of sulfuric acid and the water present in the reaction mixture, and also by increased mixture temperature. In reaction (2) the first term of the left-hand side represents the monoester of sulfuric acid salt obtained by the neutralization reaction, which salt, in the presence of the sulfur trioxide obtained from reaction (1), becomes reconverted into the initial monoester of sulfuric acid, with the formation of sodium sulfate. This second reaction is also favoured by increased reagent contact time and increased temperature.

Even if the aforesaid reactions take place in only a small part of the total mass of mixture being neutralized, the product suffers the following negative consequences:

(i) increase in the percentage of sulfated compound in the product from the neutralization stage, to the detriment of the true degree of conversion obtained in the previous sulfation stage;

(ii) increase in the NaOH consumed;

(iii) increase in the quantity of sodium sulfate present in the final product, with a consequent considerable increase in its viscosity (any viscosity increase of the product worsens stirring and heat transfer conditions, thus leading to further degradation).

Furthermore, the content of inorganic salts is related to the minimum required value for the commercial product, and must in practice be no more than 1.5-2%, compatible with the content of sulfuric acid originally present in the monoester of sulfuric acid and which is produced during the sulfation stage.

To obviate these drawbacks, represented by the above reactions (1, 2), the known state of the art provides for the use of high power mixers and large circulation pumps for cooling the mixture subjected to the neutralization process. Neutralization is therefore carried out in a plant which comprises: a high power mixer; a pump of high capacity and head; and a heat exchanger of the plate or other high efficiency type.

OBJECT OF THE INVENTION

According to the present invention neutralization is carried out in several stages in cascade, by feeding all the neutralization agent into the first stage and from here in series to the subsequent stage or stages, whereas the monoester of sulfuric acid is fed in parallel, in predetermined fractions, to the various stages.

Accordingly, the present invention provides a process for neutralizing sulfated compounds, in particular monoester of sulfuric acids deriving from the sulfation of sulfatable alcohols, carried out in at least two stages to which decreasing fractions of the compound to be neutralized are fed in parallel, whereas the entire quantity of the neutralizing agent is fed to the first stage, and from here, together with the mixture of the neutralized compound, the compound to be neutralized, and the dilution water and/or water produced during the neutralization, is fed to the subsequent reactor or reactors in series.

Preferably, the mixture of reaction products leaving each reactor (or, at least, the first reactor) is recycled continuously to the reactor in a quantity 5 to 30 times greater than the throughput of the mixture treated in the reactor. A heat exchanger is preferably included in the recycling circuit. Downstream of each reactor or, at least, downstream of the last reactor, there is preferably a pH meter which, in relation to the measured pH controls the feed of a proportioned quantity of neutralizing agent to the corresponding reactor.

In a preferred process, the neutralization stages are two in number, of which only the first stage comprises recycling of the neutralized product, in a quantity 10 to 20 times the throughput of that stage, and only the second stage, in which 5 to 15% of the neutralization process takes place, is provided with the pH meter.

BRIEF DESCRIPTION OF THE DRAWINGS

The invention will be described further, by way of example, with reference to the accompanying drawings, in which the single FIGURE diagrammatically represents a process for the two-stage neutralization of a monoester of sulfuric acid consisting of an alcohol ethylene oxide sulfate containing three moles of ethylene oxide, for producing active material having a 70% (by weight) concentration in the final product obtained.

DESCRIPTION OF THE PREFERRED EMBODIMENT

With reference to the drawing, 419 Kg/h of the monoester of sulfuric acid arrive from a sulfation stage through a conduit 10. This flow is divided between two conduits 11 and 12, the first of which feeds 85 to 95% of the total flow of monoester of sulfuric acid to a first reactor 20. All the necessary sodium hydroxide, which in this case is about 40 Kg/h diluted with about 171 Kg/h of water (from a conduit 22), reaches the first reactor 20 through a conduit 21. Thus 85 to 95% of the neutralization reaction takes place in the reactor 20.

A pump 30 withdraws the mixture being neutralized from the bottom of the first reactor 20 and recycles it through conduits 23, 24, and 25. The capacity of the pump 30 is conveniently 10-20 times the total flow rate through the conduits 11 and 21. A heat exchanger 31 maintains the temperature of the mixture in the first reaction stage in the range from about 40° C. to about 45° C.

At the outlet of the heat exchanger 31, the conduit 24 forks into two conduits 25 and 26, the former returning most of the liquid from the conduit 23 to the reactor 20, (e.g. 5670 to 6090 Kg/h), while the latter feeds only a small fraction to second reactor 40 (e.g. 567 to 601 Kg/h). The flow rate through the conduit 26 must obviously be equal, on an average, to the sum of the flow rates through the conduits 11 and 21 which feed the first reactor 20.

The second fraction of monoester of sulfuric acid to be neutralized (5 to 15% of the total flow) is fed to the second reactor 40, and the completely neutralized product leaves the reactor 40 through a conduit 41. The dimensions of the two reactors 20 and 40 are chosen such that the time for passing through the first can lie between 10 and 20 minutes, whereas the time for passing through the second is limited to 1–6 minutes.

The short traversing time through the second neutralization reactor 40 allows effective correction of the pH of the mixture leaving the second reactor to be made. In this respect, a pump 50 allows small quantities of finished product to be withdrawn from the outlet conduit 41, then to be fed to a pH meter 51, and from here to be returned to the system through a conduit 52 which opens into the recycle conduit 23. A control signal 60, depending on the measured pH value of the outlet mixture, is fed to an NaOH correction dispenser 61 which is fed from the sodium hydroxide source through a conduit 62, and which by way of a conduit 63 can feed the necessary small quantities of sodium hydroxide to the second reactor 40 for making the said correction. The dispenser 61 can also feed correcting quantities of sodium hydroxide through a conduit 64 to the first reactor 20 via the recycle conduit 23, although this procedure is generally necessary only during plant start-up.

EXAMPLE b 1

Neutralization of lauryl alcohol sulfated in a gaseous $SO_3$ sulfation plant.

Raw material: synthetic $C_{12}$–$C_{15}$ lauryl alcohol; average M.W. 207. The acid was first neutralized in the laboratory (process A) with the aid of a solvent (ethyl alcohol) under optimum conditions (control).

In a plant as described above, 350 Kg/h of active material (A.M.) were produced, diluted in $H_2O$ to a final concentration of 32% of active material (process B).

The products of these processes had the following analyses:

|  | (neutr. in laboratory) | (from plant) |
|---|---|---|
| A.M. | 30.40% | 32.60% |
| unsulfated | 0.72% | 0.75% |
| $Na_2SO_4$ | 0.33% | 0.34% |
| $H_2O$-alcohol | balance | balance |

EXAMPLE 2

Neutralization of lauryl alcohol containing three moles of ethylene oxide (Eo), sulfated with gaseous $SO_3$.

Raw material: synthetic $C_{12}$–$C_{15}$ lauryl alcohol +3EO; average M.W. 339.

The acid was first neutralized in the laboratory with the aid of a solvent (ethyl alcohol) under optimum conditions:

these comprise rapid neutralization at low concentration level to avoid uncontrolled degradation (process A). An attempt was also made (process B) to neutralize, using normal laboratory equipment, at an A.M. concentration of 70%, without the aid of a solvent (ethyl alcohol). Thirdly, in a plant as described above, about 450 Kg/h of A.M. were produced, diluted in $H_2O$ to a final concentration of 70% of A.M. (process C).

A: Analysis of sample neutralize in the laboratory at a low A.M. concentration with the aid of a solvent.
B: Analysis of the same acid sample neutralized in the laboratory at high A.M. concentration without the aid of a solvent.
C: Analysis of the same acid sample neutralized in the plant.

|  | A | B | C |
|---|---|---|---|
| A.M. | 27.5% | 66.2% | 73.3% |
| unsulfated | 0.45%(1.64%) | 4.60%(6.95%) | 1.33%(1.82%) |
| $Na_2SO_4$ | 0.28%(1.02%) | 2.10%(3.17%) | 0.82%(1.12%) |
| $H_2O$/alcohol | balance | $H_2O$ balance | $H_2O$ balance |

The unsulfated (or degraded) alcohol values and the $Na_2SO_4$ values calculated with respect to 100% of A.M. are shown in parentheses.

These values are substantially equal for processes A and C; whereas in process B the high degradation level is apparent, although the same starting acid was used for the three cases.

What I claim is:

1. A process for neutralizing a sulfated compound, comprising feeding decreasing quantities of the compound to be neutralized to at least two successive reactors in parallel, feeding to the first reactor substantially the entire quantity of neutralizing agent necessary and sufficient to neutralize the compound, and feeding the output of each reactor to the next reactor in series.

2. A process as claimed in claim 1, in which a proportion of the output of the first reactor is recycled continuously to the first reactor in a quantity of about 5 to 30 times greater than the input to the first reactor.

3. A process as claimed in claim 2, in which heat exchange is performed during recycling.

4. A process as claimed in any of claims 1 to 3, including measuring the pH of the output from the last reactor, and feeding neutralizing agent to the last reactor as a function of the measured pH.

5. A process as claimed in claim 1, using two reactors, in which about 95 to 85% of the sulfated compound is fed to the first reactor and about 5 to 15% to the second reactor, a proportion of the output of the first reactor is recycled continuously to the first reactor in a quantity of about 10 to 20 times the input to the first reactor, the pH of the output from the second reactor is measured, and neutralizing agent is fed to the second reactor as a function of the measured pH.

6. A process according to claim 1 in which said sulfated compound is a monoester of sulfuric acid derived from the sulfation of a sulfatable alcohol.

7. A process for neutralizing a monoester of sulfuric acid derived from the sulfation of a sulfatable alcohol, comprising feeding in parallel quantities of said monoester of sulfuric acid to two successive reactors, feeding to the first reactor substantially the entire quantity of neutralizing agent necessary and sufficient to neutralize said monoester of sulfuric acid and feeding the output of the first reactor to the second reactor, wherein about 95 to 85% of the said monoester of sulfuric acid is fed to the first reactor and about 5 to 15% to the second reactor, a proportion of the output of the first reactor is recycled continuously to said first reactor in a quantity about 10 to 20 times the input to said first reactor, wherein the pH of the output from the second reactor is measured, and neutralizing agent is fed to the second reactor as a function of the measured pH.

8. A process according to claim 6 or 7, wherein said sulfated alcohol is a synthetic alcohol of 12-15 carbon atoms containing three moles of ethylene oxide.

* * * * *

UNITED STATES PATENT AND TRADEMARK OFFICE
CERTIFICATE OF CORRECTION

PATENT NO. : 4,311,650

DATED : January 19, 1982

INVENTOR(S) : Giovanni Moretti

It is certified that error appears in the above-identified patent and that said Letters Patent is hereby corrected as shown below:

Please correct the Assignee Name to read as follows:

-- BALLESTRA CHIMICA S.p.A. --

Signed and Sealed this

Fourth Day of March 1986

[SEAL]

Attest:

DONALD J. QUIGG

Attesting Officer

Commissioner of Patents and Trademarks